(12) United States Patent
Leroux et al.

(10) Patent No.: US 8,124,012 B2
(45) Date of Patent: Feb. 28, 2012

(54) AIR PURIFICATION SYSTEM, METHOD FOR PURIFYING AIR INSIDE A STRUCTURE

(75) Inventors: Alain Louis Claude Leroux, Eindhoven (NL); Jacques Maria Jozef Geboers, Neerpelt (BE)

(73) Assignee: Koninklijke Philips Electronics N.V., Eindhoven (NL)

( * ) Notice: Subject to any disclaimer, the term of this patent is extended or adjusted under 35 U.S.C. 154(b) by 819 days.

(21) Appl. No.: 12/189,942

(22) Filed: Aug. 12, 2008

(65) Prior Publication Data

US 2009/0049985 A1 Feb. 26, 2009

(30) Foreign Application Priority Data

Aug. 23, 2007 (EP) .................................... 07114846

(51) Int. Cl.
*B03C 3/00* (2006.01)
(52) U.S. Cl. ............ 422/4; 422/24; 422/121; 422/186.3
(58) Field of Classification Search ................ 96/16, 79, 96/224; 250/365, 461.1, 504 R; 422/22, 422/24; 95/79, 285
See application file for complete search history.

(56) References Cited

U.S. PATENT DOCUMENTS

| | | | | |
|---|---|---|---|---|
| 5,523,057 A * | 6/1996 | Mazzilli | ......................... | 422/121 |
| 6,022,511 A * | 2/2000 | Matschke | ..................... | 422/121 |
| 6,500,387 B1 * | 12/2002 | Bigelow | ......................... | 422/24 |
| 6,627,000 B2 * | 9/2003 | Fencl et al. | ..................... | 134/1 |
| 7,820,100 B2 * | 10/2010 | Garfield et al. | .................. | 422/1 |
| 2002/0094298 A1 * | 7/2002 | Monagan | .......................... | 422/5 |
| 2004/0005251 A1 | 1/2004 | Branham | | |
| 2004/0226813 A1 * | 11/2004 | Wang | ......................... | 204/157.3 |
| 2005/0163650 A1 * | 7/2005 | Crawford et al. | ................. | 422/4 |
| 2005/0173352 A1 * | 8/2005 | Burrows et al. | ............... | 210/748 |
| 2006/0057020 A1 * | 3/2006 | Tufo | ............................... | 422/24 |
| 2006/0280660 A1 | 12/2006 | Weiss | | |

FOREIGN PATENT DOCUMENTS

| | | |
|---|---|---|
| DE | 10209191 A1 | 9/2003 |
| EP | 1584368 A1 | 10/2005 |
| JP | 2000100221 A | 4/2000 |

\* cited by examiner

*Primary Examiner* — Duane Smith
*Assistant Examiner* — Sonji Turner (57) ABSTRACT

An air purification system for a structure includes a first radiation source for generating UV-B and/or UV-C radiation and having an imaginary horizontal plane intersecting with the center of the first radiation source. The system further includes a first screen facing the first radiation source for preventing UV radiation generated by the first radiation source from radiating directly outward from the air purification system into a space below the imaginary horizontal plane. A second screen, facing the first radiation source as well as the first screen, is adjustable with respect to the first radiation source and is at least partially coated with a photocatalytic material at a surface facing the first radiation source.

13 Claims, 8 Drawing Sheets

AIR PURIFICATION SYSTEM, METHOD FOR PURIFYING AIR INSIDE A STRUCTURE

CROSS REFERENCE TO RELATED APPLICATIONS

This application claims the benefit of European Application Number EP07114846, filed Aug. 23, 2007, which is incorporated herein in whole by reference.

TECHNICAL FIELD

The invention relates to an air purification system for a structure. The invention further related to a method for purifying air inside a structure using such a system.

BACKGROUND

Air disinfection systems using germicidal UV radiation, usually in the form of UV-C radiation, are known as such. The germicidal UV radiation disinfects the air by damaging DNA which will inactivate for example, viruses, bacteria, molds, and yeast that are present in the air. Such air disinfection systems are particularly used in places where relatively many people are present for a longer time, for example in office buildings, schools, waiting rooms in hospitals and in places where there is a high risk for infection by air transmittable diseases such as isolation rooms in hospitals, shelters for homeless people, TBC clinics etc. UV based air purification systems use a layer of a photo-catalytic material that is irradiated by a UV radiation source to produce hydroxyl radicals that react with volatile organic compounds present in the air and degrade these compounds into $H_2O$ and $CO_2$ Amongst others, UV-C radiation may be generated by a low-pressure mercury vapor discharge germicidal lamp, where mercury constitutes the primary component for the generation of ultraviolet (UV) C radiation. The discharge vessel of a low-pressure mercury vapor discharge lamp is usually circular and comprises both elongate and compact embodiments. Generally, the tubular discharge vessel of compact fluorescent lamps comprises a collection of relatively short straight parts having a relatively small diameter, which straight parts are connected together by means of bridge parts or via bent parts. The means for maintaining a discharge in the discharge space may be electrodes arranged in the discharge space. Alternatively, external electrodes can be applied. External electrodes can be provided as a conductive coating at the end parts of the discharge vessel. The conductive coatings functions as a capacitive electrode, between which a discharge extends during lamp operation along the axial distance between the external electrodes.

US2006/0280660A1 discloses a photo-catalytic air purifier including a UV light source that generates heat and a photo-catalyst coated on the lamp shade. The light source irradiates the photo-catalyst. The heat generated by the light source draws ambient air between the lamp shade and the light source by convection such that the photo-catalyst is in continuous contact with the ambient air. It is a disadvantage of the air purifier according to the prior art that human beings present in the neighborhood of the purifier may be exposed to an unacceptable level of UV radiation.

DISCLOSURE OF INVENTION

It is an object of the invention to provide an air purification system that at least partially solves the above-mentioned problem.

This object is achieved with an air purification system for a structure according to the invention, comprising a first radiation source for generating UV-B and/or UV-C radiation and having an imaginary horizontal plane intersecting with the centre of the first radiation source, a first screen facing the first radiation source for preventing UV radiation generated by the first radiation source from radiating directly outward from the air purification system into a space below the imaginary horizontal plane, a second screen facing the first radiation source as well as the first screen, adjustable with respect to the first radiation source and at least partially coated with a photo-catalytic material at a surface facing the first radiation source. The first screen prevents that human beings are directly exposed to UV-C radiation since the position of the imaginary horizontal plane can be chosen such that this is equal to or higher than at eye level of a human being. During operation of the system, the second screen is adjusted with respect to the first radiation source for directing a beam of UV-C radiation generated by the first radiation source towards a ceiling and/or at least one wall of the structure, the beam of UV-C radiation having a angle $\alpha$ with the imaginary horizontal plane such that the UV-C rays reflect at least two times with the ceiling and/or the at least one wall before being radiated towards the space below the imaginary horizontal plane. The adjustment of the second screen depends on the dimensions of the structure and by making the second screen adjustable with respect to the first radiation source this adjustment can be done when installing the air purification system in the structure. During operation, part of the UV-C radiation generated by the air purification system is radiated in a sideward direction and incidences on the walls or ceiling of the room where part of the UV-C radiation is absorbed. The remaining amount of the UV-C radiation is subsequently reflected, again towards the ceiling or walls of the room. Again, an amount of the remaining UV-C radiation is absorbed and the remaining part is reflected. These latter UV-C rays may be reflected in the direction of the floor of the room. The combination of the output of UV-C radiation generated by the radiation source and the value of the reflection coefficient for UV-C radiation of the ceiling and the wall can be chosen such that the amount of UV-C radiation that is radiated to the space below the imaginary horizontal plane is sufficiently low to be acceptable for human beings. The UV-C radiation that is radiated in a sideward direction sterilizes the air inside the room. Another part of the UV-C radiation generated by the air purification system irradiates the second screen coated with a photo-catalytic material. As a result, hydroxyl radicals are produced that decompose organic compounds present close to the photo-catalytic material. The inventors have recognized that UV-C radiation itself decomposes certain organic materials by direct photolysis and the remaining parts will then be destroyed by the photo-catalytic process. The air purification system according to the invention removes this organic compound as well as other organic compounds by applying a photo-catalytic coating on the second screen. Due to the natural convection of the air inside the room, the air is purified without exposing human beings present in the room to an unacceptable level of UV-C radiation.

Another preferred embodiment of the air purification system according to the invention is characterized in that the first screen has a hemispherical shape and in that the second screen has an at least partly hemispherical shape and is movable with respect to the first radiation source in a direction perpendicular to the imaginary horizontal plane, which is an advantageous embodiment in case a substantially spherical radiation source is used.

Another preferred embodiment of the air purification system according to the invention is characterized in that the first screen has a semicircular, elongated shape and in that the second screen has an at least partly semicircular, elongated shape and is movable with respect to the first radiation source in a direction perpendicular to the imaginary horizontal plane, which is an advantageous embodiment in case a substantially elongated radiation source is used.

Another preferred embodiment of the air purification system according to the invention is characterized in that the first screen comprises a reflector for reflecting UV radiation in a direction towards the second screen. The UV-B and/or UV-C radiation reflected by the first screen is used for activating photo-catalytic reactions on a surface of the second screen facing the radiation source.

Another preferred embodiment of the air purification system according to the invention is characterized in that the first screen is at least partially coated with a photo-catalytic material at a surface facing the first radiation source, which increases the capacity for removal of contaminants from the air.

Another preferred embodiment of the air purification system according to the invention is characterized in that the first screen is a translucent screen comprising a luminescent material for converting UV-B and/or UV-C radiation that incidences on the first screen into visible light. Using one radiation source, the system additionally provides visible light.

Another preferred embodiment of the air purification system according to the invention is characterized in that the system further comprises a second radiation source for generating visible light, which allows the user to independently control the air purification and the general lighting function.

Another preferred embodiment of the air purification system according to the invention is characterized in that the second radiation source is positioned with respect to the first screen at a side facing the first radiation source and in that a surface of the first screen facing the first radiation source is specular reflective for visible light. The visible light is reflected by the first screen towards the second screen, and subsequently diffusively reflected by the photo-catalytic material towards the space below the imaginary horizontal plane.

According to the invention, a method for purifying air in a structure using an air purification system comprises the following steps: providing the air purification system inside a structure, adjusting the distance between the air purification system and a ceiling of the structure in order to position the imaginary horizontal plane at eye level of a human being or higher, adjusting the second screen with respect to the first radiation source in order to direct a beam of UV radiation generated by the first radiation source towards a ceiling and/or at least one wall of the structure, and the beam of UV radiation having a angle α with the imaginary horizontal plane such that the UV rays reflect at least two times with the ceiling and/or the at least one wall before being radiated towards the space below the imaginary horizontal plane. This method allows purification of the air inside the structure without exposing the human beings inside the structure to an unacceptable level of UV-B and/or UV-C radiation.

Another preferred embodiment of the method for purifying air in a structure is characterized in that in the step of adjusting the second screen with respect to the first radiation source, the beam of UV radiation has an angle α with the imaginary horizontal plane such that the UV rays reflect at least a first time with the at least one wall and at least a second time with the ceiling before being radiated towards the space below the imaginary horizontal plane. This method allows a further reduction of the amount of UV-B and/or UV-C radiation that is radiated to the space below the imaginary horizontal plane.

Another preferred embodiment of the method for purifying air in a structure is characterized in that the method further comprises the step of providing at least a part of the ceiling and/or the wall with a photo-catalytic material. Another preferred embodiment of the method for purifying air in a structure is characterized in that the photo-catalytic material is provided on the inner wall of cavities provided in the ceiling. As a result, the capacity for removal of contaminants from the air is increased and at the same time the reflection of UV-B and/or UV-C radiation by the ceiling to the lower part of the room is decreased.

Another preferred embodiment of the method for purifying air in a structure is characterized in that that the adjustment of the second screen with respect to the first radiation source is done according to a table provided with the air purification system showing the relation between said adjustment and the distance between the air purification system and the ceiling as well as with the distance between the air purification system and the at least one wall. The table allows an easy and reliable installation of the air purification system inside the structure.

BRIEF DESCRIPTION OF DRAWINGS

FIGS. 1 to 7 are purely diagrammatic and not drawn to scale. Notably, some dimensions are shown strongly exaggerated for the sake of clarity. Similar components in the Figures are denoted as much as possible by the same reference numerals.

DESCRIPTION OF PREFERRED EMBODIMENTS

Figure 1:
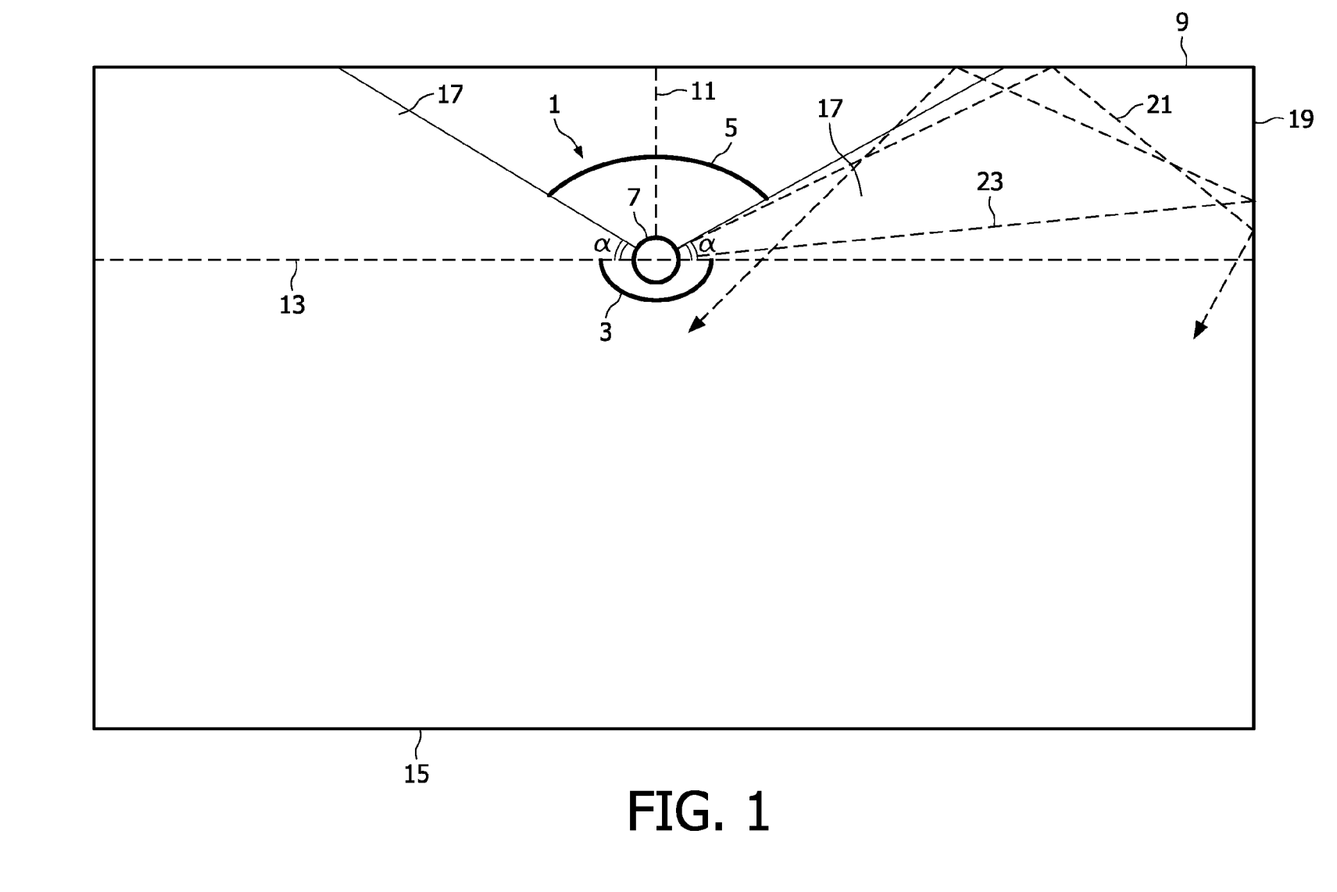
FIG. 1 is a cross-sectional and a schematic view of a first embodiment of an air purification system according to the invention.

Referring to FIG. 1, a cross-sectional and schematic drawing of an embodiment of an air purification system 1 according to the invention is shown. The air purification system 1 comprises a lower screen 3, an upper screen 5 and a radiation source 7 for generating UV-C radiation, i.e. radiation in a wavelength range of 280 nm to 200 nm or less. In an alternative embodiment, the radiation source 7 is arranged for generating UV-B radiation, i.e. radiation in a wavelength range of 280-320 nm. In a further alternative embodiment, the radiation source 7 is arranged for generating both UV-B and UV-C radiation. The air purification system 1 is suspended from the ceiling 9 of a structure, for example a hospital room, conference room, or a class room, to name a few. The lower screen 3, upper screen 5 and radiation source 7 are coupled to each other in a way known to the person skilled in the art to form a robust device, and the upper screen 5 is movable with respect to the radiation 7 along a vertical axis 11. The radiation source 7 has an imaginary horizontal plane 13 intersecting with the centre of the radiation source 7 that has a substantially spherical shape. The lower screen 3 has a hemispherical shape and the aperture of the lower screen 3 coincides with the imaginary horizontal plane 13. Furthermore, the surface of the lower screen 3 facing the radiation source 7 is coated with a material highly reflective for UV-C radiation, for example magnesium oxide (MgO), aluminum (Al) or calcium carbonate ($CaCO_3$). The upper screen 5 has a partly hemispherical shape and is coated on a surface facing the radiation source 7 with a photo-catalytic material. During operation, the air purification system 1 is suspended from the ceiling 9 such that the imaginary horizontal plane 13 is equal to or above eye level of a human being standing on the floor 15 of the structure. The lower screen 3 prevents that UV-C radiation generated by the radiation source 7 radiates directly outward from the air purification system 1 to the space below the imaginary horizontal plane 13, as this UV-C radiation is reflected by the lower screen 3 in the direction of the upper screen 5. The UV-C radiation that incidences on the surface of the upper screen 5 is absorbed by the photo-catalytic material resulting in the formation of reactive hydroxyl (OH) radicals. When a contaminant in the ambient air contacts the photo-catalytic material, the hydroxyl radical reacts with the contaminant to produce water and carbon dioxide. The photo-catalytic material may comprise titanium dioxide ($TiO_2$), tin oxide ($SnO_2$), zinc oxide (ZnO), potassium tantalum oxide ($KTaO_2$) and calcium titanate ($CaTiO_3$), to name a few. In a preferred embodiment, the photo-catalytic material consists of $TiO_2$. The UV-C radiation that not directly incidences on the lower screen 3 or the upper screen 5 is radiated outside the air purification system 1 to generate a beam 17 of UV-C radiation having an angle α with the imaginary horizontal plane 13. The upper screen 5 is positioned with respect to the radiation source 7 such that UV-C rays on the upper edge of the beam 17 incidence on the ceiling 9. UV-C rays that are not absorbed are reflected by the ceiling 9, at least partly in the direction of a wall 19 of the structure depending on whether the reflection is specular, diffusive or in between. In addition, the upper screen 5 is positioned such that these specularly reflected UV-C rays incidence on the wall above the position at the wall 19 where the imaginary horizontal plane 11 intersects with the wall 19. Subsequently, UV-C rays that are not absorbed by the wall 19 are reflected in the direction of the imaginary horizontal plane 13, as indicated by UV-C ray 21. UV-C rays on the lower edge of the beam 17 incidence on the wall 19. UV-C rays that are not absorbed are reflected by the wall 19, at least partly in the direction of the ceiling 9, again depending on whether the reflection is specular, diffusive or in between. Subsequently, UV-C rays that are not absorbed by the ceiling 9 are reflected in the direction of the imaginary horizontal plane 13, as indicated by UV-C ray 23. As a result, UV-C radiation that is radiated to the space in the structure below the imaginary horizontal plane 13 has at least reflected twice by the ceiling 9 and the wall 19, which is only a relatively small part of the UV-C radiation originally present in the beam 17; the exact amount of which depends on, amongst others, the reflection coefficient for UV-C radiation of the ceiling 9 and the wall 19. The combination of the output of UV-C radiation generated by the radiation source 7 and the value of the reflection coefficient for UV-C radiation of the ceiling 9 and the wall 19 should be such that the amount of UV-C radiation that is radiated to the space below the imaginary horizontal plane 13 is sufficiently low to be acceptable for human beings. The parts of the ceiling 9 and the wall 19 where the UV-C radiation incidences preferably have a reflection coefficient for UV-C radiation of 0.1 or lower, i.e. at least 90% of the UV-C radiation that incidences on the ceiling 9 or the wall 19 is absorbed, meaning that less than 1% of the UV-C radiation as generated by the beam 17 is radiated into the space of the structure below the imaginary horizontal plane 13 in case of specular reflection. In case of diffusive reflection the amount of light that is reflected by the ceiling 9 or wall 19 under an angle identical with the angle of incidence, as in case of specular reflection, is less, i.e. about 3% in case of a reflection coefficient of 0.1. A reflection coefficient of 0.1 or lower can be obtained by choice of the material for construction of the ceiling 9 and wall 19, or by coating at least a part of the ceiling 9 and wall 19 with a UV-C absorbing material. For the ceiling 9, plates with holes can be installed, for example, where UV-C radiation is absorbed in the holes by multiple reflections. The function of the air purification system 1 is two-fold. Firstly, the UV-C radiation present in the beam 17 disinfects the air present in the space of the structure above the imaginary horizontal plane 13. Secondly, the photo-catalytic material present on the surface of the upper screen 5 that is activated the UV-C generation removes organic contaminants from the air. Due to free convection of the air, all the air inside the structure is eventually purified, without exposing human beings present in the structure to an unacceptable level of UV-C radiation. Since the upper screen 5 is movable with respect to the radiation source 7, the position of the upper screen 5 can easily be adapted depending on, for example, the size of the ceiling 9 of the structure such that UV-C rays reflect at least two times with the ceiling 9 and/or wall 19 before being radiated towards the space below the imaginary horizontal plane 13. In an alternative embodiment, the surface of the lower screen 3 facing the radiation source 7 is coated with a photo-catalytic material, increasing the capacity of the air purification system for removal of contaminants from the air. In another alternative embodiment, the surface of the upper screen 5 facing the radiation source 7 may be partially coated with a photo-catalytic material while the other parts of the surface facing the radiation source 7 are coated with another UV-C absorbing material. In an alternative embodiment, the lower screen 3 has an semicircular, elongated shape and the upper screen 5 has an partly semicircular, elongated shape. The latter embodiment is preferred in case of an elongated radiation source 7.

Figure 2:
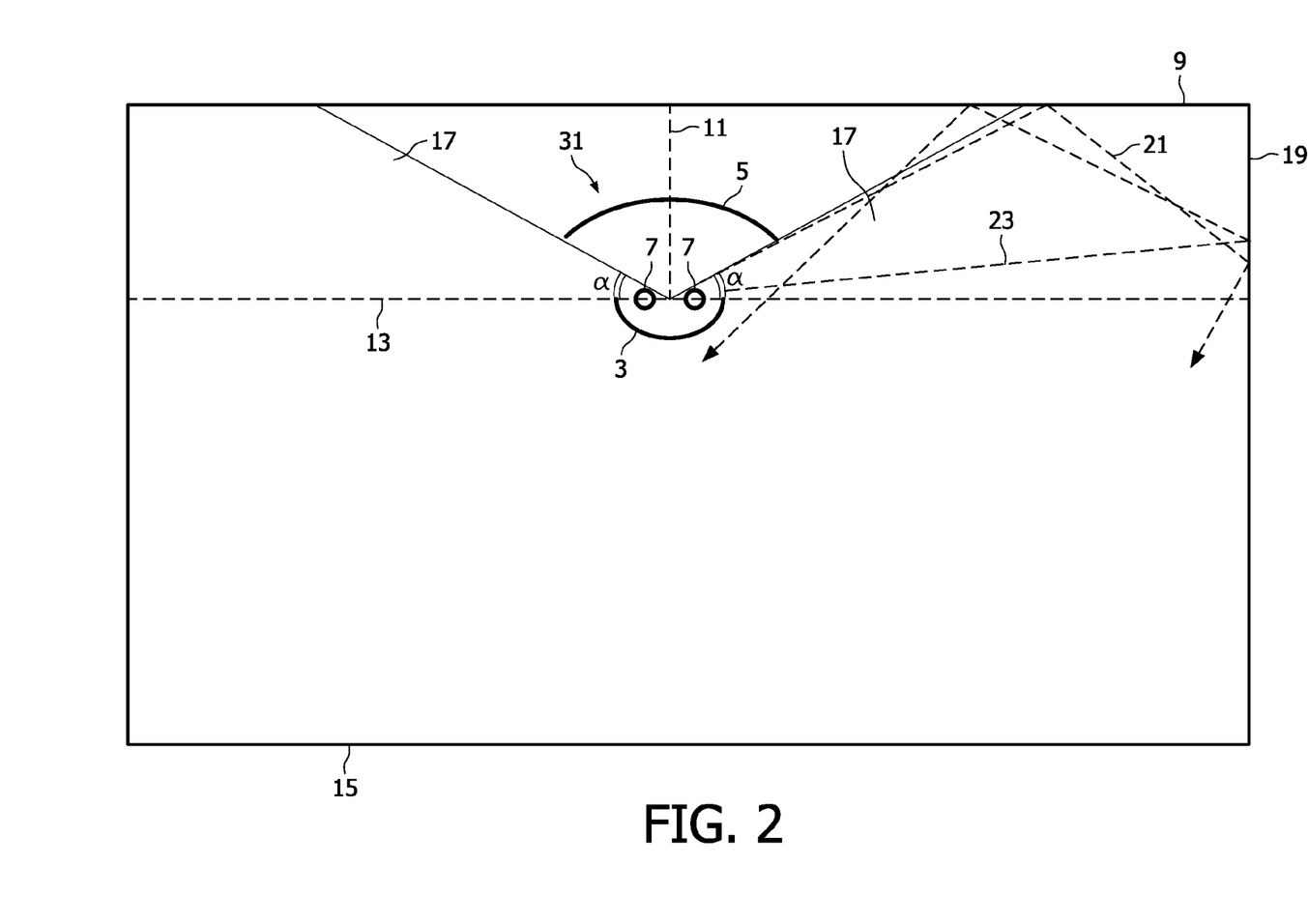
FIG. 2 is a cross-sectional and a schematic view of a second embodiment of an air purification system according to the invention.

Referring to FIG. 2, a cross-sectional and schematic drawing of an alternative embodiment of an air purification system according to the invention is shown. Components corresponding to those in FIG. 1 have an identical reference numeral. The air purification system 31 comprises two radiation sources 7 for generating UV-C radiation. The imaginary horizontal plane 11 intersects the centre of both radiation sources 7. The two radiation sources 7 can be operated independently meaning that the degree of air purification can be adapted according to the circumstances.

Figure 3:
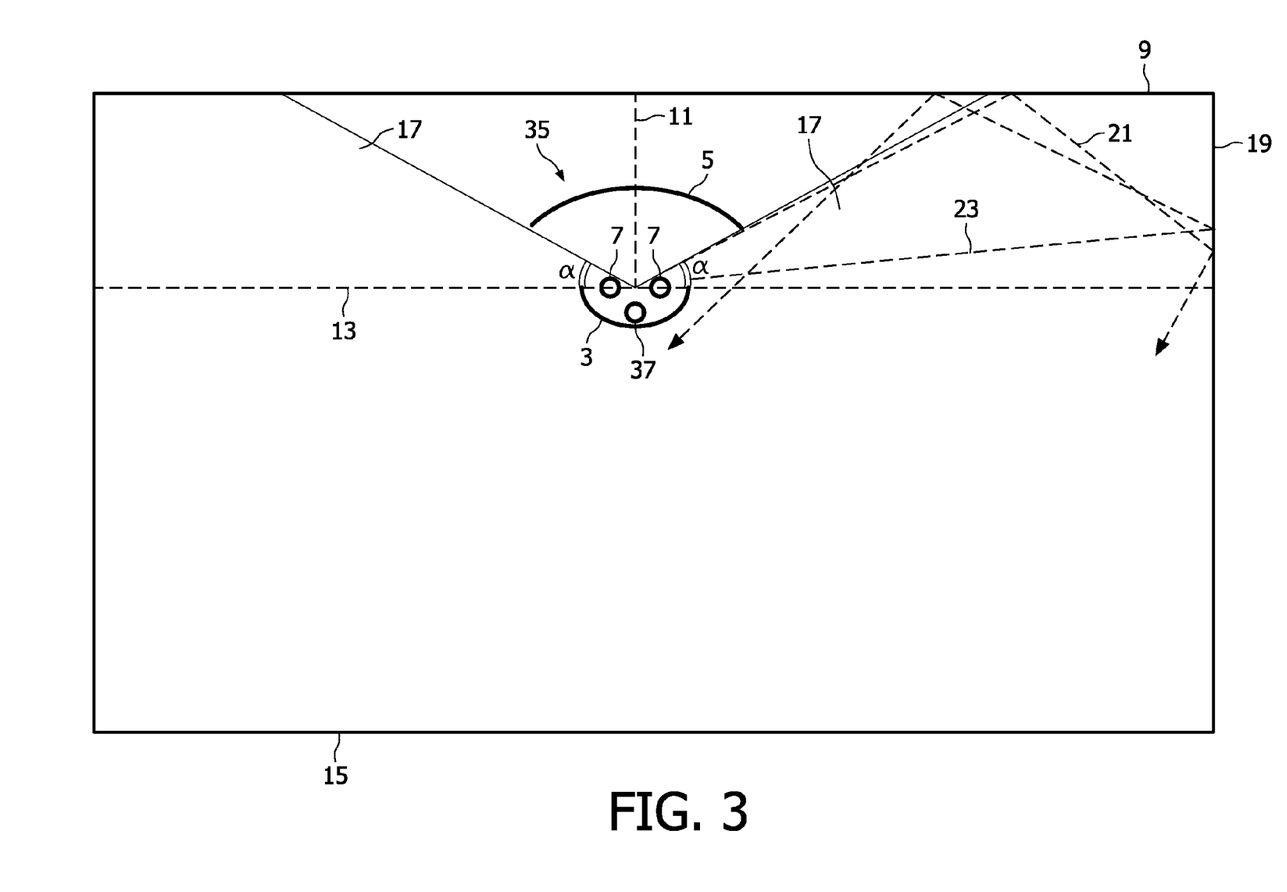
FIG. 3 is a cross-sectional and a schematic view of a third embodiment of an air purification system according to the invention.

Referring to FIG. 3, a cross-sectional and schematic drawing of a further alternative embodiment of an air purification system according to the invention is shown. Components corresponding to those in FIG. 2 have an identical reference numeral. The air purification system 35 comprises two radiation sources 7 for generating UV-C radiation as well as a radiation source 37 for generating visible light. The radiation sources 7, 37 can all be operated independently. The surface of the lower screen 3 is reflective for both UV-C and visible radiation. The photo-catalytic material on the surface of the upper screen 7 is diffusive reflective for visible radiation by nature, and as a result the visible light generated by radiation source 37 is diffusively reflected to the space below the imaginary horizontal plane 13. Compared to the air purification systems shown in FIG. 1 and 2, the air purification system 35 can additionally be used for general lighting purposes. Radiation source 37 can be any source for generating visible light, for example a gas discharge lamp or an (organic) light emitting diode.

Figure 4:
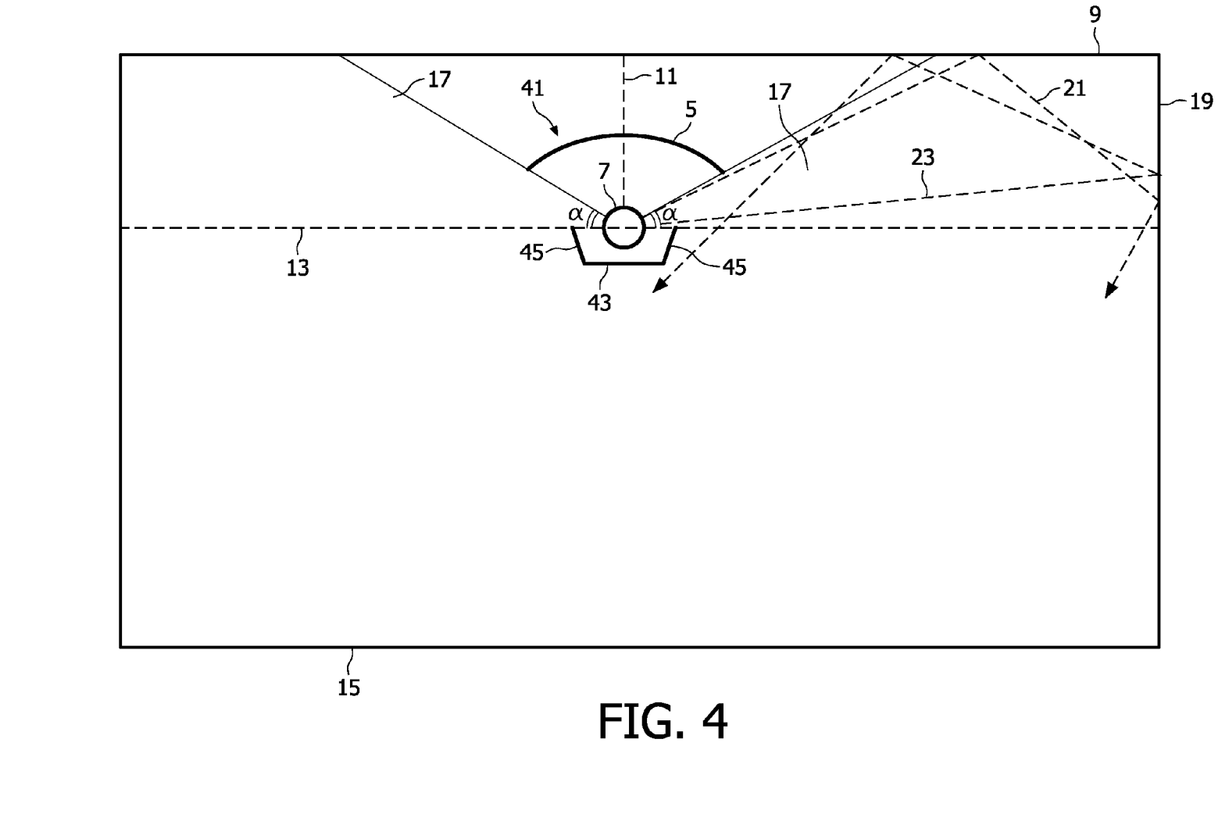
FIG. 4 is a cross-sectional and a schematic view of a fourth embodiment of an air purification system according to the invention.

Referring to FIG. 4, a cross-sectional and schematic drawing of a further alternative embodiment of an air purification system according to the invention is shown. Components corresponding to those in FIG. 1 have an identical reference numeral. The air purification system 41 comprises a lower screen 43 with a horizontal part in the middle and four raised edges 45, not all shown in FIG. 4. The lower screen 43 comprises a translucent material, such as quartz ($SiO_2$) glass or any other glass used for mercury gas discharge lamps. The surface of the lower screen 43 facing the radiation source 7 is coated with a luminescent material, for example a combination of a phosphor for generating blue light ($BaMgAl_{10}O_7$:$Eu^{2+}$), a phosphor for generating green light ($CeMgAl_{11}O_{19}$:$Tb^{3+}$) and a phosphor for generating red light ($Y_2O_3$:$Eu^{3+}$), resulting in substantially white light, or any other (combination of) luminescent material(s) used for general lighting. The luminescent material absorbs UV-C radiation that incidences on the material to generate visible light that is radiated towards the space of the structure below the imaginary horizontal plane 13. The air purification system 41 combines the function of air purification with that of general lighting. By providing a sufficient thick layer of luminescent material for absorbing all UV-C radiation, or alternatively by providing a lower screen 43 comprising a translucent material that is blocking UV-C radiation, it is prevented that UV-C radiation passes through the lower screen 43.

Figure 5:
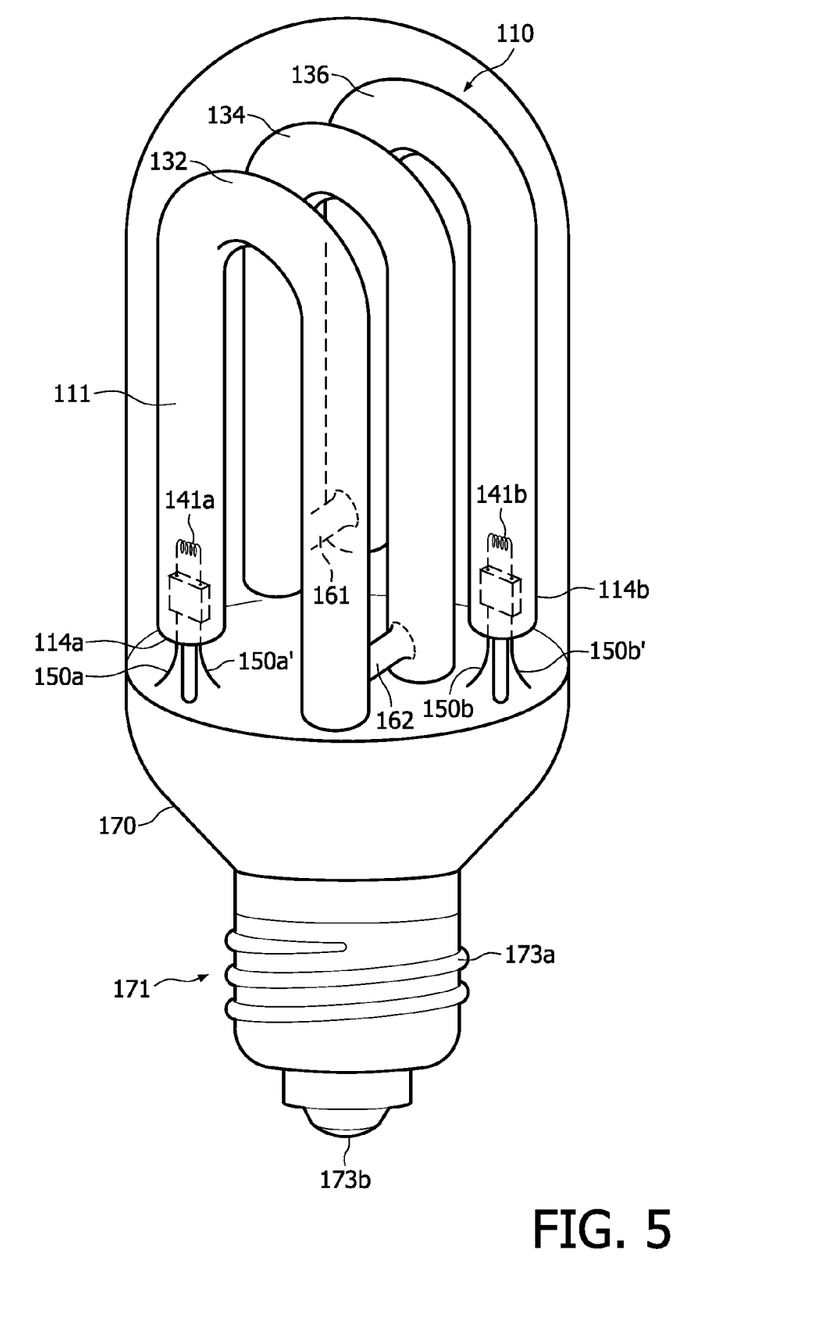
FIG. 5 is a cross-sectional and a schematic view of a first embodiment of a low-pressure mercury vapor discharge lamp.

FIG. 5 is a cross-sectional and a schematic view of an embodiment of a low-pressure mercury vapor discharge lamp is shown that can be used as a radiation source 7 for generating UV-C radiation. The discharge lamp comprises a radiation-transmissive discharge vessel 110 which encloses a discharge space 111 in a gastight manner. In this case, the discharge vessel 110 comprises a mixture of 75% by volume of argon and 25% by volume of neon, with a filling pressure of 400 Pa. In this embodiment, the discharge vessel 110 is formed from a light-transmissive tubular portion of lime glass having three U-shaped segment 132, 134, 136. The discharge vessel 110 is sealed by end portions 114a; 114b. The segments 132, 134, 136 are interconnected by (tubular) ducts 161, 162. Means for maintaining a discharge are constituted by an electrode pair 141a; 141b arranged in the discharge space 111. The electrode pair 141a; 141b is a winding of tungsten coated with an electron-emissive material (emitter material), in this case a mixture of barium, calcium and strontium oxide. Each electrode 141a; 141b is supported by an end portion 114a; 114b of the discharge vessel 10. Current supply conductors 150a, 150a'; 150b, 150b' project from the electrode pair 141a; 141b through the end portion 114a; 114b of the discharge vessel 110. The current supply conductors 150a, 150a', 150b, 150b' are connected to a power supply (not shown) incorporated in the housing 170 and electrically connected to known electrical and mechanical contacts 173a, 173b on the lamp base 171. The discharge space 11 comprises, in addition to the rare gas mixture, mercury. The centre of the discharge lamp is defined as the geometric centre of the discharge vessel 110.

Figure 6:
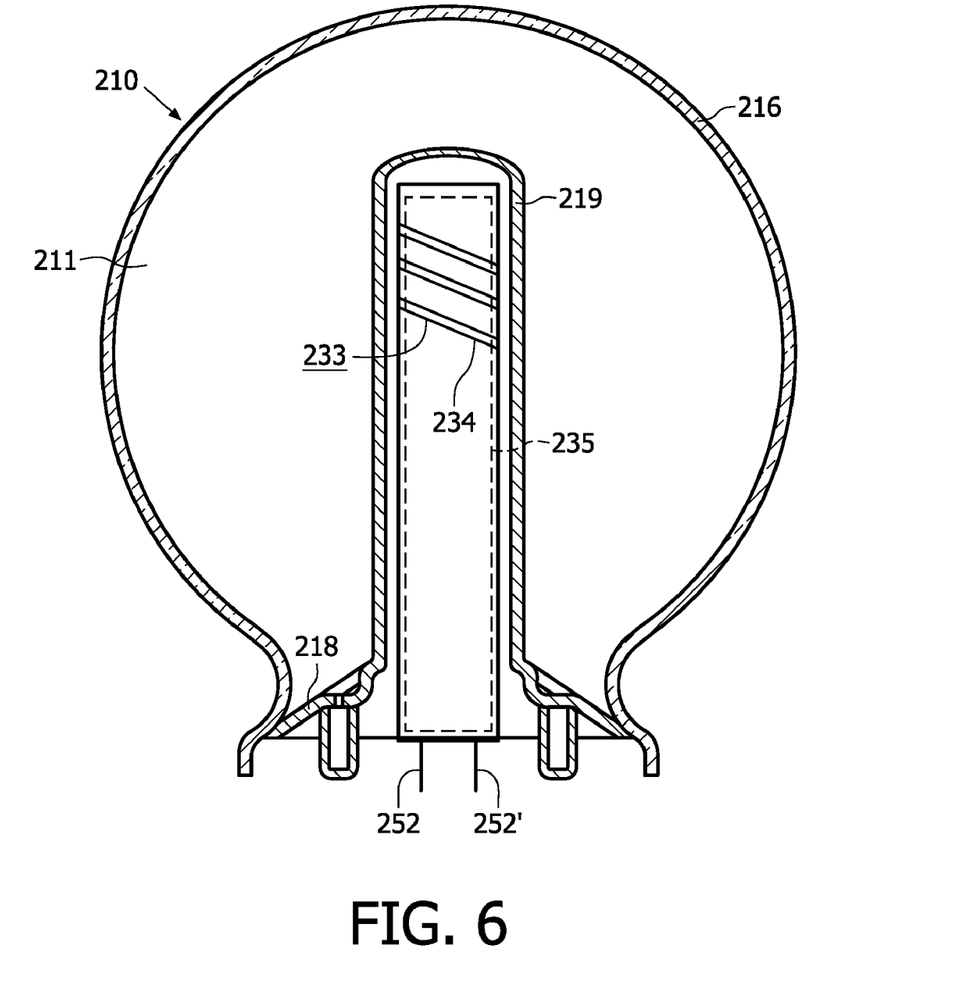
FIG. 6 is a cross-sectional and a schematic view of a second embodiment of a low-pressure mercury vapor discharge lamp

Referring to FIG. 6, an alternative embodiment of a low-pressure mercury vapor discharge lamp is shown that can be used as a radiation source 7 for generating UV-C radiation. Components corresponding to those in FIG. 5 have a reference numeral increased by 100. The discharge vessel 210 has a pear-shaped enveloping portion 216 and a tubular invaginated portion 219 that is connected to the enveloping portion 216 via a flared portion 218. The invaginated portion 219, outside a discharge space 211 surrounded by the discharge vessel 210, accommodates a coil 233 which has a winding 234 of an electric conductor constituting means for maintaining an electric discharge in the discharge space 211. The coil 233 is fed via current supply conductors 252, 252' with a high-frequency voltage during operation, i.e. a frequency of approximately 20 kHz or more, typically 3 MHz. The coil 233 surrounds a core of a soft-magnetic material (shown in broken lines). Alternatively, the core may be omitted. In an alternative embodiment the coil 233 is arranged inside the discharge space 211. The centre of the discharge lamp is defined as the geometric centre of the discharge vessel 210.

Figure 7:
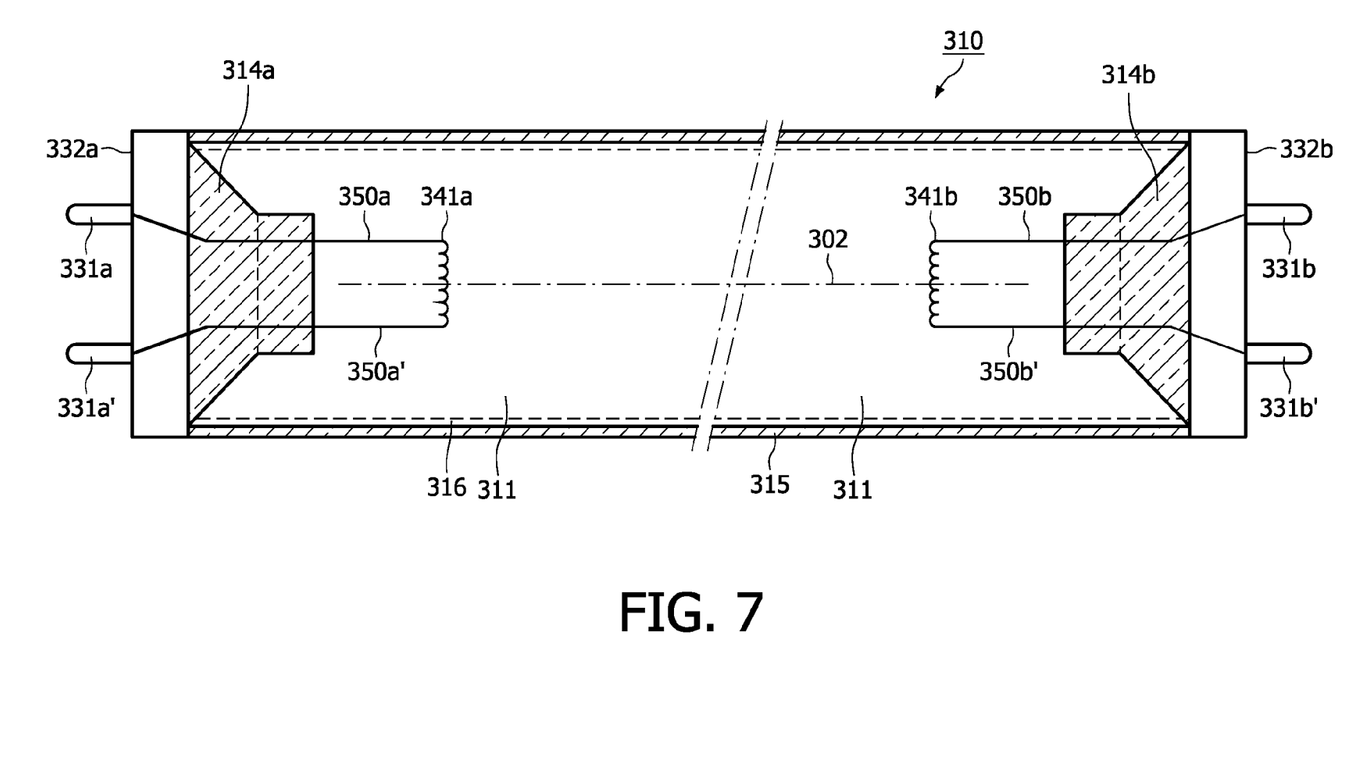
FIG. 7 is a cross-sectional and a schematic view of a third embodiment of a low-pressure mercury vapor discharge lamp.

Referring to FIG. 7, a further alternative embodiment of a low-pressure mercury vapor discharge lamp is shown that can be used as a radiation source 7 for generating UV-C radiation. Components corresponding to those in FIG. 5 have a reference numeral increased by 200. The lamp has a glass discharge vessel 310 having a tubular portion 315 about a longitudinal axis 302 and enclosing a discharge space 311. The discharge vessel 310 transmits radiation generated in the discharge space 311 and is provided with a first and a second end portion 314a; 314b, respectively. The discharge vessel 310 encloses, in a gastight manner, a discharge space 311 containing a filling of mercury and an inert gas mixture comprising for example argon. In the example of FIG. 7, the side of the tubular portion 315 facing the discharge space 311 is provided with a protective layer 316. In the example of FIG. 7 means for maintaining a discharge in the discharge space 311 are electrodes 341a; 341b arranged in the discharge space 311, said electrodes 341a; 341b being supported by the end portions 314a; 314b. The electrode 341a; 341b is a winding of tungsten covered with an electron-emitting substance, in this case a mixture of barium oxide, calcium oxide and strontium oxide. Current-supply conductors 350a, 350a'; 350b, 350b' are connected to contact pins 331a, 331a'; 331b, 330b' secured to lamp cap 332a, 332b. The centre of the discharge lamp is defined as the geometric centre of the discharge vessel 310.

Alternatively, the radiation source 7 for generating UV-C generation is an (organic) light emitting diode, or a high pressure mercury vapor discharge lamp.

Figure 8:
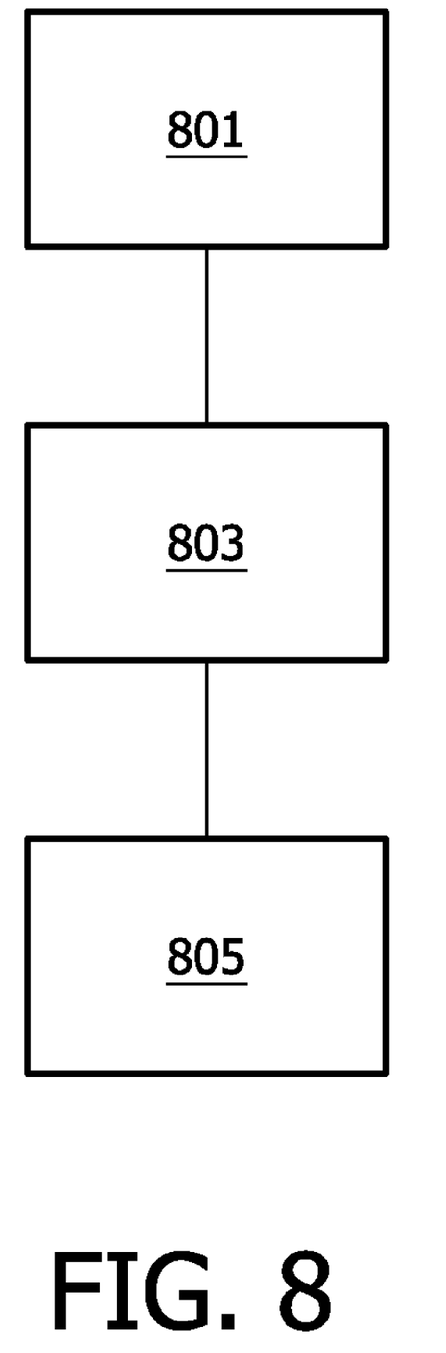
FIG. 8 shows a method for purifying air inside a structure according to the invention.

Referring to FIG. 8, a method for purifying air inside a structure using an air purification system according to FIG. 1 is shown. In a first step 801 the air purification system 1 is provided inside a structure, e.g. a hospital room, living room, conference room or class room, to name a few. In a second step 803, the distance between the air purification system 1 and a ceiling 9 of the structure is adjusted in order to position the imaginary horizontal plane 13 at eye level of a human being, typically 1.80 meter, or higher. In a third step 805, the upper screen 5 is adjusted with respect to the radiation source 7 in order to direct a beam 17 of UV-C radiation towards the ceiling 9 and the wall 19, the beam 17 having an angle α with the imaginary horizontal plane 13 such that the UV-C rays reflect at least two times with the ceiling 9 and/or the at least one wall 19 before being radiated towards the space below the imaginary horizontal plane 13. For a given air purification system 1 the exact adjustment of the upper screen 5 with respect to the radiation source 7 depends on the distance between the air purification system 1 and the ceiling 9 as well as on the distance between the air purification system 1 and the wall 19. In a further embodiment of the method, the adjustment of the upper screen 5 with respect to the radiation source 7 is done according to a table provided with the air purification system 1 showing the relation with the distance between the air purification system 1 and the ceiling 9 as well as with the distance between the air purification system 1 and the wall 19. In an alternative embodiment of the method, the beam of UV-C radiation 17 has an angle α with the imaginary horizontal plane 11 such that the UV-C rays reflect at least a first time with the wall 19 and at least a second time with the ceiling 9 before being radiated towards the space below the imaginary horizontal plane 11. In another further embodiment of the method, the method further comprises a step to provide at least a part of the ceiling 9 and/or the wall 19 with a photo-catalytic material. The UV-C radiation that incidences on the wall 19 or the ceiling 19 activates the photo-catalytic material which further increases the capacity to remove contaminants from the air. In addition, the amount of UV-C radiation that is reflected to the lower part of the structure is further reduced. In another further embodiment of the method, the ceiling 9 is provided with cavities of which the inner walls are provided with a photo-catalytic material. In another further embodiment of the method, an air purification system is used that generates UV-B radiation only, or alternatively a combination of UV-B and UV-C radiation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An air purification system for a structure, comprising:
   a first radiation source for generating UV radiation and having an imaginary horizontal plane intersecting with a center of the first radiation source,
   a first screen facing the first radiation source for preventing the UV radiation generated by the first radiation source from radiating directly outward from the air purification system into a space below the imaginary horizontal-plane plane;
   a second screen facing the first radiation source and the first screen, and being at least partially coated with a photo-catalytic material at a surface facing the first radiation source, wherein the second screen is adjustable with respect to the first radiation source by moving the second screen towards or away from the imaginary horizontal plane such that the UV radiation reflects at least two times with a ceiling and/or at least one wall of the structure before being radiated towards the space below the imaginary horizontal plane.

2. The system according to claim 1, wherein the first screen has a hemispherical shape, and wherein the second screen has an at least partly hemispherical shape and is movable with respect to the first radiation source in a direction perpendicular to the imaginary horizontal plane.

3. The system according to claim 1, wherein the first screen has a semicircular, elongated shape, and wherein the second screen has an at least partly semicircular, elongated shape and is movable with respect to the first radiation source in a direction perpendicular to the imaginary horizontal plane.

4. The system according to claim 2, wherein the first screen comprises a reflector for reflecting the UV radiation in a direction towards the second screen.

5. The system according to claim 1, wherein the first screen is at least partially coated with a photo-catalytic material at a surface facing the first radiation source.

6. The system according to claim 1, wherein the first screen is a translucent screen comprising a luminescent material for converting the UV radiation that is incident on the first screen into visible light.

7. The system according to claim 1, further comprising a second radiation source for generating visible light.

8. The system according to claim 7, wherein the second radiation source is positioned with respect to the first screen at a side facing the first radiation source, and wherein a surface of the first screen facing the first radiation source is specular reflective for the visible light.

9. A method for purifying air inside a structure using an air purification system having a radiation source for generating UV radiation and having an imaginary horizontal plane intersecting with a center of the radiation source, the method comprising the act of:
   providing the air purification system inside a structure;
   adjusting a distance between the air purification system and a ceiling of the structure in order to position the imaginary horizontal plane at eye level of a human being or, higher;
   adjusting the second screen with respect to the first radiation source in order to direct a UV beam of the UV radiation generated by the first radiation source towards a ceiling and/or at least one wall of the structure, and the UV beam having a angle α with the imaginary horizontal plane such that the UV beam reflects at least two times with the ceiling and/or the at least one wall before being radiated towards a space below the imaginary horizontal plane.

10. The method according to claim 9, wherein in the act of adjusting the second screen with respect to the first radiation source, the UV beam has an angle α with the imaginary horizontal plane such that the UV beam reflects at least a first time with the at least one wall and at least a second time with the ceiling before being radiated towards the space below the imaginary horizontal plane.

11. The method according to claim 9,
   further comprising the act of providing at least a part of the ceiling and/or the wall with a photo-catalytic material.

12. The method according to claim 11, wherein the photo-catalytic material is provided on an inner wall of cavities provided in the ceiling.

13. The method according to claim 9, wherein the adjusting act is done according to a table provided with the air purification system showing a relation between adjustment of the second screen and the distance between the air purification system and the ceiling as well as with the distance between the air purification system and the at least one wall.

* * * * *